(12) United States Patent
Goldsberry et al.

(10) Patent No.: US 10,124,030 B2
(45) Date of Patent: Nov. 13, 2018

(54) SKINCARE PREPARATIONS

(71) Applicant: KARYNG, LLC, Santa Monica, CA (US)

(72) Inventors: Susan Goldsberry, Irvine, CA (US); Karyn Grossman, Santa Monica, CA (US)

(73) Assignee: KARYNG, LLC, Santa Monica, CA (US)

( * ) Notice: Subject to any disclaimer, the term of this patent is extended or adjusted under 35 U.S.C. 154(b) by 16 days.

(21) Appl. No.: 15/497,134

(22) Filed: Apr. 25, 2017

(65) Prior Publication Data

US 2017/0304371 A1 Oct. 26, 2017

Related U.S. Application Data

(60) Provisional application No. 62/327,232, filed on Apr. 25, 2016.

(51) Int. Cl.
| | | |
|---|---|---|
| *A61K 36/00* | (2006.01) | |
| *A61K 36/28* | (2006.01) | |
| *A61K 31/045* | (2006.01) | |
| *A61K 31/4166* | (2006.01) | |
| *A61K 9/00* | (2006.01) | |
| *A61K 36/185* | (2006.01) | |
| *A61K 36/51* | (2006.01) | |
| *A61K 8/9789* | (2017.01) | |

(52) U.S. Cl.
CPC ............ *A61K 36/28* (2013.01); *A61K 8/9789* (2017.08); *A61K 9/0014* (2013.01); *A61K 31/045* (2013.01); *A61K 31/4166* (2013.01); *A61K 36/185* (2013.01); *A61K 36/51* (2013.01)

(58) Field of Classification Search
CPC ..................................................... A61K 36/00
USPC ......................................................... 424/725
See application file for complete search history.

(56) References Cited

FOREIGN PATENT DOCUMENTS

| CN | 101396429 A | * | 4/2009 |
|---|---|---|---|
| WO | WO 2015/136198 A1 | | 9/2015 |

OTHER PUBLICATIONS

Unknown, NET-DG, product bulletin and technical paper by Barnet Products, 2011, 2 pp.
Unknown, Drago-Calm Natural anti-irritant with Anti-Histaminic Properties, presentation material, date unknown, by Symrise GmbH & Co. AG, Germany, 24 pp.
Unknown, MAXnolia Protects Skin Against Inflammatory Aging, product brochure by Mibelle Biochemistry, 2009, Switzerland, 15 pp.
Unknown, SymRepair (153884), product brochure by Symrise GmbH & Co. AG, Germany, date unknown, 26 pp.
Unknown, SymVital, product brochure by Symrise GmbH & Co. AG, Germany, date unknown, 34 pp.
Unknown, NEODERMYL, product brochure and technical paper by Induchem Companies, date unknown, 7 pp.
Unknown, Inula® SC, product brochure by Biotech Marine, date unknown, 10 pp.
Unknown, AC Collagen PrePeptide, product brochure by Active Concepts, 2006, 1 sheet.
Unknown, CENTEROX® product brochure by Indena S.p.A., Italy, date unknown, 2 pp.
Unknown, SymFinity® 1298 product brochure by Symrise GmbH & Co. AG, date unknown, 46 pp.
Unknown, Progeline™ product brochure Lucas Meyer Cosmetics, USA, date unknown, 20 pp.
Unknown, SWT-7™ product brochure by Lucas Meyer Cosmetics, USA, date unknown, 32 pp.
Unknown, Hydrolite® 5, product brochure by Symrise GmbH & Co. AG, Germany, date unknown, 1 sheet.
Unknown, Transcutol® CG PHYTOREAM® 2000, NANOCREAM®, HITECREAM® 3000, and EWOCREAM® available from Gattefossé SAS, France, product brochure and technical paper, date unknown, 15 pp.
Unknown, Neosolue-Aqulio available from Nippon Fine Chemical Co., Ltd., Japan, product brochure, 2008, 19 pp.
Unknown, SEPILIFT™ DPHP available from SEPPIC S.A., France, product brochure, date unknown, 6 pp.
Unknown, EMUL-SIN Sinerga Emulsifiers Solutions available from Sinerga, Italy, product brochure, date unknown, 12 pp.
Unknown, OPEXTAN® available from Indena S.p.A., Italy, product brochure, date unknown, 26 pp.
Unknown, Superox-C™ available from Lucas Meyer Cosmetics, USA, product brochure, 4 pages.
Majeed, M et al., Soy Isoflavins, Technical Paper, date unknown, 2 pp.
Unknown, Gatuline® Age Defense available from Gattefossé SAS, product brochure, date unknown, 19 pp.
Unknown, ARGIRELINE® Peptide available from Lipotec SAU, Spain, product brochure, 2013, 21 pp.
Unknown, Snap-8 available from Lipotec SAU, Spain, product brochure, date unknown, 2 pp.
Unknown, Dolcévia® available fromm Sinerga S.p.A., Italy, product brochure, date unknown, 2 pp.
Unknown, p-REFINYL® available from Silab, France, product brochure, 2016, 2 pp.

(Continued)

*Primary Examiner* — Michael V Meller
(74) *Attorney, Agent, or Firm* — Lewis Roca Rothgerber Christie LLP

(57) ABSTRACT

An active constituent complex includes an active carrier, an anti-inflammatory agent, a collagen synthesis enhancer, an anti-wrinkle agent, and a keratinocyte growth factor stimulant. The active constituent complex may be incorporated into a skincare composition, such as for topical application to human skin, for promoting skin repair and restructure, and for treating skin conditions.

20 Claims, No Drawings

(56) References Cited

OTHER PUBLICATIONS

Unknown, Eyeliss™ available from Sederma, France, product brochure, date unknown, 2 pp.
Unknown, Rosamox™ available from Kemin Industries, USA, product brochure, date unknown, 4 pp.
Unknown, AcquaCell available from Barnet Products Corp, USA, product brochure, date unknown, 2 pp.

* cited by examiner

SKINCARE PREPARATIONS

CROSS-REFERENCE TO RELATED APPLICATION(S)

This application claims priority to and the benefit of U.S. Provisional Application No. 62/327,232, filed Apr. 25, 2016 and titled SKINCARE PREPARATIONS, the entire content of which is incorporated herein by reference.

BACKGROUND

The skin is an organ of the body that performs vital functions including protection against external physical, chemical, and biologic aggressions. The skin is made up of three layers: the epidermis, the dermis, and hypodermis. The epidermis is the outermost part of the skin. The middle layer, the dermis, is basically made up of the fibrous structural protein called collagen, and it is a connective tissue of fibroblasts and an extracellular matrix that functions to provide cohesion and nutrition to the skin. The dermis lies on the hypodermis, which includes adipocytes, connective tissue, and elastins, providing an energy reservoir and thermal protection.

The epidermis includes several cell layers composed primarily of keratinocytes. The epidermis harbors other cell populations such as dendritic cells, melanocytes, Langerhans cells, and Merkel cells, but keratinocytes by far make up the majority of the cells. The epidermis is commonly divided into four layers: the basal layer (stratum germinativum), the spinous layer (stratum spinosum), the granular layer (stratum granulosum), and the cornified or horny layer (stratum corneum).

Human skin is continually being renewed. The outermost cells of the horny layer are continually desquamated and replaced by cells of a lower layer by a cellular process of epidermis renewal undertaken by keratinocytes. The cells that form at the basal layer through mitosis progressively differentiate and migrate (move up) through the layers of the skin to reach the horny layer. As the cells move up the strata, they generate keratin, a fibrous protein that is water insoluble, and which progressively fills the cells. As they move towards the upper layers, the keratinocytes degenerate and secrete a cement, which increases cohesion between the cells, thereby effectively creating a waterproof barrier over the body's surface.

Skin aging follows a normal process of senescence which may be exacerbated by external factors such as exposure to ultraviolet radiation from the sun. With aging, the epidermis thins, even though the number of cell layers may remain unchanged. Large pigmented spots may appear in sun-exposed areas. Changes in the connective tissue reduce the skin's strength and elasticity.

Aesthetically, these changes in the skin due to aging or external factors result in a change in the appearance of the skin. The skin may appear rough or less smooth, may develop more lines or wrinkles, and/or may show stretch marks and redness. Additionally, the skin may lose elasticity and firmness, and/or skin complexion may appear less luminous.

Many existing cosmetic products on the market purport to prevent or reduce wrinkles, redness, or stretch marks. However, many of these products entail lengthy waiting periods before visible results are achieved, are simply less effective than claimed, or not effective at all. Additionally, to achieve effective anti-aging performance, a regimen of several different skincare products is typically required.

SUMMARY

According to embodiments of the present invention, a cosmetic composition, for example a skincare preparation, is capable of promoting the repair and restructure of skin. In some embodiments, for example, an active constituent complex includes active ingredients for promoting skin repair and restructure. According to some embodiments, the active constituent complex can be incorporated into a skincare composition, such as for topical application to human skin. Some nonlimiting examples of such skincare compositions include cleansers (e.g., facial or body cleansers), serums, creams (including night creams and day creams with or without sun protection additives), etc.

According to embodiments of the present invention, the active constituent complex includes an active carrier, an anti-inflammatory agent, a collagen synthesis enhancer, an anti-wrinkle agent, and a keratinocyte growth factor stimulant. In some embodiments, for example, the active carrier may include an aqueous solvent or an organic solvent, for example, alcohol such as ethanol, propanediol, butylene glycol, isopropanol, glycerin, or a mixture thereof. In some embodiments, the active carrier may include Pentylene Glycol, Ethoxydiglycol, Bis-Ethoxydiglycol Cyclohexane 1,4-Dicarboxylate, Dipalmitoyl Hydroxyproline, Potassium Palmitoyl Hydrolyzed Wheat Protein, Glyceryl Stearate, Cetearyl Alcohol, Potassium Lauroyl Wheat Amino Acids, Palm Glycerides, Capryloyl Glycine, Potassium Palmitoyl Hydrolyzed Oat Protein, Behenyl Alcohol, Palm Glycerides, Sodium Stearoyl Glutamate, Sucrose Palmitate, Polyglyceryl-3 Sorbityl Linseedate, or a combination thereof. According to some embodiments, the anti-inflammatory agent may include alpha-Bisabolol, Allantoin, Sea Whip Extract, *Chamomilla Recutita* (*Matricaria*) Extract, Tocopheryl Acetate, *Camellia Sinensis* Leaf Extract, *Curcuma Longa* (Turmeric) Root Extract, *Avena Sativa* (Oat) Kernel Extract, *Magnolia Officinalis* Bark Extract, *Vitis Vinifera* (Grape) Seed Extract, *Zingiber Officinale* (Ginger) Root Extract, Dipotassium Glycyrrhizinate or "DPG" ($C_{42}H_{60}K_2O_{16}$), or a combination thereof. In some embodiments, the collagen synthesis enhancer may include Methylglucoside Phosphate, *Inula Crithmoide* Flower/Leaf Extract, Collagen Prepeptide (e.g., G-P-Hyp tripeptide), Madecassoside, Asiaticoside, or a combination thereof. According to some embodiments, the anti-wrinkle agent may include an *Echinacea Purpurea* Extract, Cichoric acid, Resveratrol, Trifluoroacetyl Tripeptide-2, or a combination thereof. In some embodiments, the keratinocyte growth factor stimulant may include a purified form (purity of at least 95%) or an enriched extract of swertiamarin.

According to embodiments of the present invention, the active constituent complex can be incorporated into, and provided in, various compositions, such as in the form of emulsions (e.g., creams), gels, lotions, repairing cleansers, serums, eye creams, night moisturizers, and day lotions. The compositions may also be in anhydrous forms, such as in the form of ointments, gels, or serums.

According to some embodiments, the active constituent complex is incorporated into a repairing cleanser. In some embodiments, the repairing cleanser of the present invention may include about 0.5-1.5 wt % of the active constituent complex. For example, in some embodiments, the active constituent complex may be present in the repairing cleanser in an amount of about 1.04 wt % based on the total weight of the repairing cleanser. For example, according to some embodiments the cleanser may contain cosmeceutically effective amounts of one or more of the following constituents: Dipotassium Glycyrrhizinate, Pentylene Glycol, Glycerin (and) Water (and) Methylglucoside Phosphate (and) Copper Lysinate/Prolinate, *Echinacea Purpurea* Extract, Isopropyl Palmitate (and) Lecithin (and) Water (and) *Swertia Chirata* Extract, Glycerin, and Sodium Hydroxide.

According to some embodiments, the active constituent complex is incorporated into a serum. In some embodiments, the serum may include about 2.0-4.5 wt % of the active constituent complex. For example, in some embodiments, the active constituent complex may be present in the serum in an amount of about 3.7 wt % based on the total weight of the serum. For example, in some embodiments, the serum may contain cosmeceutically effective amounts of one or more of the following constituents: Dipotassium Glycyrrhizinate, Pentylene Glycol, Glycerin (and) Water (and) Methylglucoside Phosphate (and) Copper Lysinate/Prolinate, *Echinacea Purpurea* Extract, Isopropyl Palmitate (and) Lecithin (and) Water (and) *Swertia Chirata* Extract, *Glycine Soja* Oil, Aqua, Glycerin, Cera Alba, Retinol, Laureth-23, Trideceth-6 Phosphate, Phenoxyethanol, Triethanolamine, Ceramide-3, and *Lens Esculenta* (Lentil) Seed Extract.

According to some embodiments, the active constituent complex is incorporated into an eye cream. In some embodiments, the eye cream may include about 2.0-4.5 wt % of the active constituent complex. For example, in some embodiments, the active constituent complex may be present in the eye cream in an amount of about 3.8 wt % based on the total weight of the eye cream. For example, in some embodiments, the eye cream may contain cosmeceutically effective amounts of one or more of the following constituents: Dipotassium Glycyrrhizinate, Pentylene Glycol, Glycerin (and) Water (and) Methylglucoside Phosphate (and) Copper Lysinate/Prolinate, *Echinacea Purpurea* Extract, Isopropyl Palmitate (and) Lecithin (and) Water (and) *Swertia Chirata* Extract, Glycerin, *Butyrospermum Parkii* (Shea) Butter, Niacinamide, Sodium Hydroxide, Steareth-20, N-Hydroxysuccinimide, Chrysin, Palmitoyl Oligopeptide, Palmitoyl Tetrapeptide-7, Hesperidin Methyl Chalcone, and Dipeptide-2.

According to some embodiments, the active constituent complex is incorporated into a night moisturizer. In some embodiments, the night moisturizer may include about 2.0-4.5 wt % of the active constituent complex. For example, in some embodiments, the active constituent complex may be present in the night moisturizer in an amount of about 3.8 wt % based on the total weight of the night moisturizer. For example, in some embodiments, the night moisturizer may contain cosmeceutically effective amounts of one or more of the following constituents: Dipotassium Glycyrrhizinate, Pentylene Glycol, Glycerin (and) Water (and) Methylglucoside Phosphate (and) Copper Lysinate/Prolinate, *Echinacea Purpurea* Extract, Isopropyl Palmitate (and) Lecithin (and) Water (and) *Swertia Chirata* Extract, Glycerin, *Butyrospermum Parkii* (Shea) Butter, Xylitylglucoside, Anhydroxylitol, Xylitol, *Helianthus Annuus* (Sunflower) Seed Oil (and) *Rosmarinus Officinalis* (Rosemary) Leaf Extract, *Citrullus lanatus* (Watermelon) Fruit Extract, Lens *Esculenta* (Lentil) Fruit Extract, *Pyrus Malus* (Apple) Fruit Extract, Sodium PCA, Sodium Lactate, and Sodium Hyaluronate. In some embodiments, the night moisturizer may include EPIDERMOSIL available from Exsymol, Monaco.

According to some embodiments, the active constituent complex is incorporated into a day/daily lotion (day and daily are used interchangeably). In some embodiments, the daily lotion may include about 2.0-4.5 wt % of the active constituent complex. For example, in some embodiments, the active constituent complex may be present in the daily lotion in an amount of about 3.8 wt % based on the total weight of the daily lotion. For example, in some embodiments, the daily lotion may contain cosmeceutically effective amounts of one or more of the following constituents: Dipotassium Glycyrrhizinate, Pentylene Glycol, Glycerin (and) Water (and) Methylglucoside Phosphate (and) Copper Lysinate/Prolinate, *Echinacea Purpurea* Extract, Isopropyl Palmitate (and) Lecithin (and) Water (and) *Swertia Chirata* Extract, Titanium Dioxide, Zinc Oxide, and Glycerin.

DETAILED DESCRIPTION

When incorporated into a skincare composition, the active constituent complex according to embodiments of the present invention promotes skin repair and restructure. Additionally, as discussed herein, the active constituents in the active constituent complex may exhibit a synergistic effect, yielding unexpectedly superior promotion of skin repair and restructure over an unexpectedly reduced period of time.

For example, the active constituent complex according to some embodiments of the present invention can increase the quantity of total collagen in skin by about 4 to 8% after only about 6 to 15 days of treatment. In some embodiments, for example, the active constituent complex can increase the quantity of total collagen in skin by about 5 to 7% after only about 7 to 12 days of treatment. For example, in some embodiments, the active constituent complex may increase the quantity of total collagen by about 6.8% after only 11 days of treatment.

Additionally, according to some embodiments, the active constituent complex can increase elastin production in skin by about 80 to 250% after only about 10 to 12 days of treatment. In some embodiments, for example, the active constituent complex can increase elastin production in skin by about 120 to 220% after only about 10 to 12 days of treatment. For example, in some embodiments, the active constituent complex may increase elastin production by about 190% after only about 11 days of treatment.

Moreover, the active constituent complex according to some embodiments of the present invention can more quickly reduce wrinkle depth, for example by about 5 to 30% after treatment for only about 7 to 30 days. In some embodiments, for example, the active constituent complex can reduce wrinkle depth by about 10 to 20% after treatment for only about 10 to 20 days. For example, in some embodiments, the active constituent complex can reduce wrinkle depth by about 15% after treatment for only about 15 days.

Further, the active constituent complex according to some embodiments of the present invention can reduce the appearance of wrinkles by about 40 to 70% after treatment for only about 5 to 15 days, and/or reduce skin roughness by about 30 to 60% after treatment for only about 5 to 15 days, thereby promoting even skin tone and texture. In some embodiments, for example, the active constituent complex may reduce the appearance of wrinkles by about 50 to 60% after treatment for only about 5 to 10 days, and/or reduce skin roughness by about 40 to 50% after treatment for only about 5 to 10 days. For example, in some embodiments, the active constituent complex may reduce the appearance of wrinkles by about 53% after treatment for only 7 days, and/or reduce skin roughness by about 42% after treatment for only 7 days.

The active constituent complex according to some embodiments of the present invention can repair skin from deep within the cellular level, by diffusing into the skin (e.g., when topically applied), re-energizing senescent fibroblasts, and triggering essential elements to produce collagens and elastin.

In some embodiments, the active constituent complex according to some embodiments of the present invention can impart anti-inflammatory, anti-oxidant, redness reduction effect to skin, or a combination thereof.

The active constituent complex according to some embodiments of the present invention can prolong longevity of skin cells by increasing their resilience to stress, boost DNA repair from UV-B induced damage, and improve the cell's detoxification process.

As discussed above, according to embodiments of the present invention, the active constituent complex includes an anti-inflammatory agent. The anti-inflammatory agent is an agent that serves to provide an anti-inflammatory effect, and it may also provide anti-hyaluronidase activity, UV-erythema reduction, inhibition of histamine release, an effect on arachidonic cascade ($LTB_4$, $PGE_2$), antifungal effect, antibacterial effect, anti-oxidant effect, anti-aging effect, anti-irritant effect, anti-itch effect, or a combination thereof. In some embodiments, the anti-inflammatory agent may be selected from those that exhibit anti-hyaluronidase activity. In some embodiments, the anti-inflammatory agent may be water-soluble, or may be approved for quasi-drug applications. In some embodiments, the anti-inflammatory agent may contain naturally-derived material, a synthetically-derived material, or a combination thereof. Non-limiting examples of the anti-inflammatory agent include alpha-Bisabolol, Allantoin, Sea Whip Extract, *Chamomilla Recutita* (*Matricaria*) Extract, Tocopheryl Acetate, *Camellia Sinensis* Leaf Extract, *Curcuma Longa* (Turmeric) Root Extract, *Avena Sativa* (Oat) Kernel Extract, *Magnolia Officinalis* Bark Extract, *Vitis Vinifera* (Grape) Seed Extract, *Zingiber Officinale* (Ginger) Root Extract, DPG, and combinations thereof. DPG may be extracted from licorice root. A non-limiting example of a suitable anti-inflammatory agent includes NET-DG available from Barnet Products Corporation, NJ, USA, and described in the NET-DG product brochure available from Barnet Products and attached as an Appendix to U.S. Provisional Application No. 62/327,232, the entire content of which product brochure, provisional application and Appendix is incorporated herein by reference. Other non-limiting examples of suitable anti-inflammatory agents include Drago-Calm, SymRepair (153884), and SymVital® AgeRepair available from Symrise AG, Germany, and MAXnolia available from Mibelle Biochemistry, Switzerland, which are described in their respective product brochures from Symrise AG and Mibelle Biochemistry and attached as an Appendix to U.S. Provisional Application No. 62/327,232, the entire content of which I product brochures, provisional application and Appendix are incorporated herein by reference.

Hyaluronidase is thought to be activated during inflammation of the skin, which plays a role in the destruction of the connective tissue matrix and the increase in permeability of the inflammatory cells and blood vessels. According to embodiments of the present invention, the anti-inflammatory agent may impart anti-hyaluronidase activity to the active constituent complex. For example, Barnet Products has reported that 3.4 µg/ml of NET-DG may inhibit 50% of Hyaluronidase activity, as described in the NET-DG product brochure available from Barnet Products and attached as an Appendix to U.S. Provisional Application No. 62/327,232, the entire content of which is incorporated herein by reference.

The anti-inflammatory agent may also reduce inflammation or stinging sensations. For example, Barnet Products has reported that use of a cream with 0.2% NET-DG reduces the stinging sensation (on a scale of 0 to 2) by more than a factor of 2, and described in the NET-DG product brochure available from Barnet Products and attached as an Appendix to U.S. Provisional Application No. 62/327,232, the entire content of which is incorporated herein by reference. In particular, Barnet Products reports testing 6 patients split in 2 groups. The patients washed their faces, and 20 minutes later, applied a cream with 5% lactic acid with or without 0.2% NET-DG. The second group performed similar operations but in reverse order, i.e., they applied the cream first, and then washed their faces. All patients received the same treatment but in a different sequence (blind test). The patients reported a reduction in stinging sensation when using the cream including NET-DG by more than a factor of 2, and described in the NET-DG product brochure available from Barnet Products and attached as an Appendix to U.S. Provisional Application No. 62/327,232, the entire content of which is incorporated herein by reference.

In some embodiments, the active constituent complex of the present invention may include about 0.5-6.0 wt % of the anti-inflammatory agent. In some embodiments, the active constituent complex of the present invention may include about 0.8-5.5 wt % of the anti-inflammatory agent. For example, in some embodiments, the anti-inflammatory agent may be present in the active constituent complex in an amount of about 0.96 wt %, 2.70 wt %, or 5.26 wt % based on the total weight of the active constituent complex.

As discussed above, the active constituent complex according to embodiments of the present invention also includes a collagen synthesis enhancer. A collagen synthesis enhancer enhances, activates, or promotes collagen and elastin production in skin. In some embodiments, the collagen synthesis enhancer may include a bio-energy source, which may further include methyl-glucoside-6-phosphate and copper. Bio-energy is required to drive the production of collagen and elastin. However, loss of bio-energy occurs with aging, and skin cells are no longer able to produce collagen and elastin effectively. The extracellular matrix (ECM) is composed of these essential polymers, which provide the skin with its structural and biochemical support, and physiological properties. Young skin is supple, firm, and elastic. These polymers include different types of collagens (mainly collagens I and III) that maintain skin's structure, and elastins that provide the skin with viscoelasticity.

Enzymes such as collagenases and peptidases degrade the collagen and elastin as a result of aging. This is especially true for collagen III, a youth collagen, which degrades even faster than collagen I and almost disappears with age. Also, with aging, the senescent cells (fibroblasts) lose their ability to produce the essential polymers at a pace sufficient to compensate for the loss. This failure to compensate for the loss of the essential polymers in the ECM is believed to be due to the loss of energy required to drive the production. As a result, the skin forms wrinkles, and loses firmness and elasticity. The collagen synthesis enhancer provides a source of energy to feed the aging skin cells to reactivate collagen and elastin production. In some embodiments, for example, the collagen synthesis enhancer includes copper, which reactivates lysyl oxidase, the enzyme that allows maturation of collagen and elastin.

According to embodiments of the present invention, the collagen synthesis enhancer may include methyl-glucoside-6-phosphate and copper as well as one or more essential amino acids that play a major role in the production of collagen and elastin that the body is no longer able to produce by itself. Non-limiting examples of these essential amino acids include proline and lysine. Non-limiting examples of the collagen synthesis enhancer according to embodiments of the present invention include Methylglucoside Phosphate, *Inula Crithmoide* Flower/Leaf Extract, Collagen Prepeptide (e.g., G-P-Hyp tripeptide), Madecassoside, Asiaticoside, and combinations thereof. A non-limiting example of a suitable collagen synthesis enhancer is Neodermyl® available from Induchem AG, Germany, and described in the Neodermyl product brochure available from Induchem AG and attached as an Appendix to U.S. Provisional Application No. 62/327,232, the entire content of which product brochure, provisional application and Appendix is incorporated herein by reference. Other non-limiting examples of suitable collagen synthesis enhancers include Inula® SC available from SEPPIC S.A., France; AC Collagen PrePeptide available from Active Concepts, USA; and CENTEROX® available from Indena S.p.A., Italy, which are described in their respective product brochures available from SEPPIC S.A., Active Concepts, USA, and Indena S.p.A. and attached as an Appendix to U.S. Provisional Application No. 62/327,232, the entire content of which product brochures, provisional application and Appendix are incorporated herein by reference.

According to embodiments of the active constituent complex, the collagen synthesis enhancer can increase the quantity of total collagen, and elastin production. In some embodiments, the collagen synthesis enhancer may act as an anti-wrinkle agent.

For example, Induchem AG has reported that Neodermyl® can increase the quantity of total collagen in skin by 6.8% after 11 days of treating the skin with the product. In particular, Induchem AG reports an ex vivo test, where human skin explants were treated with Neodermyl® at day 0, day 1, day 4, day 6, and day 8. The treated skin explants were then sampled and analyzed for total collagen production by microscopial observation and image analysis at day 0, day 6, and day 11. Induchem AG found that the quantity of total collagen increased by 6.8% in 11 days, as described in the Neodermyl product brochure available from Induchem AG and attached as an Appendix to U.S. Provisional Application No. 62/327,232, the entire content of which product brochure, provisional application and Appendix is incorporated herein by reference.

Induchem AG also reported, for example, that Neodermyl® can increase elastin production in skin by 190% after 11 days of treating the skin with the product. In particular, after studying the total collagen on the skin explants as described above, Induchem AG quantitatively evaluated the action of elastin production by immunostaining elastin, and found that the elastin production increased in the skin by 190% in 11 days, described in the Neodermyl product brochure available from Induchem AG and attached as an Appendix to U.S. Provisional Application No. 62/327,232, the entire content of which product brochure, provisional application and Appendix is incorporated herein by reference.

The collagen synthesis enhancer according to some embodiments of the present invention can increase skin firmness and elasticity. The collagen synthesis enhancer according to some embodiments can reduce wrinkle depth and volume.

For example, Induchem AG has reported that Neodermyl® can increase skin firmness by 13 times and elasticity by 1.6 times after 15 days. In particular, Induchem AG reports a double-blind test versus placebo under dermatological control with twenty volunteers 61+/−7 years old. The volunteers applied the placebo on one side of the face, and a cream containing Neodermyl® at 1% on the other side of the face twice per day. Collagen density and anisotropy index were measured using SIAscopy and SkinEvidence™ visio image analysis (Laboratoires la Licorne, France), respectively. The two parameters, R0 and R5, were measured by Cutometry to evaluate the performance of Neodermyl® at 1% on firmness and elasticity. Wrinkle depth and volume were measured by silicone replica and calculated using the Dermatop® system (Sanofi-Aventis U.S. LLC) and Toposurf® software (Somicronic, Lyon, France). Induchem AG reported that using Neodermyl® at 1%: 1) increases firmness by 13 times and elasticity by 1.6 times in only 15 days, and that these improvements in skin parameters were sustained after two months of treatment; and 2) reduces wrinkle depth by 15% and wrinkle volume by 13% in only 15 days.

In some embodiments, the active constituent complex may include about 0.5-35 wt % of the collagen synthesis enhancer. In some embodiments, the active constituent complex may include about 0.8-30 wt % of the collagen synthesis enhancer. For example, in some embodiments, the collagen synthesis enhancer may be present in the active constituent complex in an amount of about 0.96 wt %, 26.32 wt %, or 27.03 wt % based on the total weight of the active constituent complex.

Additionally, as discussed above, according to embodiments of the present invention, the active constituent complex includes an anti-wrinkle agent. An anti-wrinkle agent is an agent that exhibits anti-wrinkle efficacy, such as a reduction of wrinkles or fine lines including wrinkle depth or volume, smoothing of the skin surface, reductions in sagging skin, increased radiance of the skin, reductions in age spots, reductions in dark circles around the eyes, increased skin density, increased firmness of the skin, enhancement of skin tone, and/or increased elasticity of the skin. In some embodiments, the anti-wrinkle agent may be a SIRT1 activator, which may include Cichoric acid as an ingredient. Excessive exposure to sunlight (ultraviolet radiation) is believed to cause chronic skin damage and change, such as wrinkles, irregular pigmentation, and collagenous degeneration including damage of the deoxyribonucleic acid (DNA) of the cells. DNA contains genetic material which is necessary for replication of the genetically coded hereditary dispositions during cell division. Intense or prolonged exposure of skin to sunlight can lead to changes in the structure of the DNA in the epidermis, such as DNA cyclobutane dimers, DNA strand breaks, DNA crosslinks, DNA-protein crosslinks and 6-4 photoproducts. Such changes in the structure of the DNA can lead to cell death or inheritable cell damage.

To maintain genetic integrity, however, each cell possesses an endogenous defense system, in which several cellular responses are activated, including mechanisms for removal of DNA damage, cell cycle arrest, and apoptosis. Sirtuin (silent mating type information regulation 2 homolog) 1 is a NAD-dependent protein that is encoded by the SIRT1 gene, and Sirtuin 1 is believed to play an important role in cell defense and survival in response to stress such as that from solar radiation. SIRT1 is an enzyme that deacetylates proteins that contribute to cellular regulation. SIRT1 is expressed in the skin in the epidermis and cultured keratinocytes, in the dermis and cultured fibroblasts, and in the white adipose tissue and cultured preadipocytes and adipocytes. According to embodiments of the present invention, the anti-wrinkle agent that includes a SIRT1 activator in the active constituent complex is believed to provide anti-aging benefits and prolong cell life. Resveratrol, a polyphenol from grapes, is the most well-known SIRT1 activator.

Non-limiting examples of the anti-wrinkle agent according to embodiments of the present invention include *Echinacea Purpurea* Extract, Cichoric acid, Resveratrol, Trifluoroacetyl Tripeptide-2, and combinations thereof. A non-limiting example of a suitable anti-wrinkle agent, e.g., an SIRT1 activator, includes SymFinity®1298 available from Symrise AG, Germany, described in the SymFinity® product brochure available from Symrise AG and attached as an Appendix to U.S. Provisional Application No. 62/327,232, the entire content of which product brochure, provisional application and Appendix is incorporated herein by reference. Another non-limiting example of a suitable anti-wrinkle agent is Progeline™ available from Lucas Meyer Cosmetics, USA, described in the Progeline™ product brochure available from Lucas Meyer Cosmetics, USA and attached as an Appendix to U.S. Provisional Application No. 62/327,232, the entire content of which product brochure, provisional application and Appendix is incorporated herein by reference. Other non-limiting examples of the anti-wrinkle agent include ARGIRELINE® peptide and snap-8 available from Lipotec SAU, Spain; and Dolcévia® available from Sinerga S.p.A., Italy, described in their respective product brochures available from Lipotec SAU and Sinerga S.p.A. and attached as an Appendix to U.S. Provisional Application No. 62/327,232, the entire content of which product brochures, provisional application and Appendix is incorporated herein by reference.

In some embodiments of the active constituent complex, the anti-wrinkle agent can exhibit the following functions: reduced wrinkles; prolonged longevity of skin cells by increasing their resilience to stress, such as by boosting DNA repair from UV-B induced damage and improving the cell's detoxification process; anti-inflammatory, antimicrobial, anti-oxidant, and/or wound healing effects; stimulated immune system; or combinations thereof.

For example, Symrise AG has reported that SymFinity® can significantly induce an anti-wrinkle effect of 10% on average on day 28 in 72% of the tested subjects, and 12% on average on day 56 in 67% of the tested subjects. In particular, Symrise AG reports an in vivo test, where 2 groups of 22 women in parallel (one group getting a placebo and the other getting SymFinity®1298 0.1%), aged between 45 and 65 and having wrinkles, fine lines, or crow's feet, were treated with SymFinity®1298 twice daily for 2 months. Using Primos PICA® (before/after), Symrise AG analyzed the following cutaneous relief parameters:

Ra: the average roughness in µm. A decrease in this parameter characterizes a smoothing effect.

Rz: the average relief: average of all peak-to-valley heights.

Rt: the relief amplitude: average of the 5 maximum peak-to-valley height.

A decrease in one of these parameters (Rt and Rz) characterizes an anti-wrinkle effect of the product. The results reported by Symrise AG are as shown below in Table 1.

TABLE 1

| | Placebo | | SymFinity ®1298 | |
| --- | --- | --- | --- | --- |
| | Day 28 | Day 56 | Day 28 | Day 56 |
| Ra | No variation | 9% of efficacy 57% of subjects | 9% of efficacy 61% of subjects | 12% of efficacy 56% of subjects |
| Rz | No variation | No variation | 10% of efficacy 72% of subjects | 12% of efficacy 67% of subjects |
| Rt | No variation | No variation | 5% of efficacy 61% of subjects | 8% of efficacy 61% of subjects |

Symrise AG has also reported, for example, that after only 2 days, SymFinity®1298 significantly improves skin's own ability to resist stress such as that from UVB irradiation. In particular, Symrise AG conducted an ex vivo study with the following protocol:

Study Protocol 6 skin explants (average diameter: 10 mm) per treatment

Application of 2 µg formulation (hydrodispersion gel) per explant and treatment

Treatment once daily on day 0, 1 and 2 (15 min before irradiation)

Day 2: 3 of the 6 explants per treatment were irradiated with UVB at dose of 0.2 J/cm$^2$, the other 3 explants remained unirradiated Day 3: explants were collected and fixed in buffered formaldehyde solution After 24 h fixation, explants were dehydrated and impregnated in paraffin 5 µm thick sections of the explants imbedded in paraffin were made and bonded on superfrost silanized histological glass slides SIRT1 was stained with an anti-SIRT1 polyclonal antibody with a biotin/streptavidin enhancement system and revealed by VIP (Vector SK-4600)

For image analysis of immunostaining of SIRT1, 9 microscopic fields were digitalized and analyzed per treatment The results of modulation of epidermal SIRT1 protein expression, as reported by Symrise AG, are shown below in Table 2.

TABLE 2

| Untreated with UVB vs no UVB | Placebo vs untreated with UVB | 0.02% Resveratrol vs untreated with UVB | 0.06% SymFinity ®1298 vs untreated with UVB |
| --- | --- | --- | --- |
| 587% | −14% | −22% | −38% |

In some embodiments, the active constituent complex may include about 0.5-3.5 wt % of the anti-wrinkle agent. In some embodiments, the active constituent complex may include about 0.8-3.0 wt % of the anti-wrinkle agent. For example, in some embodiments, the anti-wrinkle agent may be present in the active constituent complex in an amount of about 0.96 wt %, 2.63 wt %, or 2.70 wt % based on the total weight of the active constituent complex.

As discussed above, according to embodiments of the present invention, the active constituent complex includes a keratinocyte growth factor stimulant. A keratinocyte growth factor stimulant is a bioactive substance that stimulates the production of keratinocyte growth factor in skin. The keratinocyte growth factor stimulant may include swertiamarin (CAS: 17388-39-5).

The chemical formula of swertiamarin is as follows:

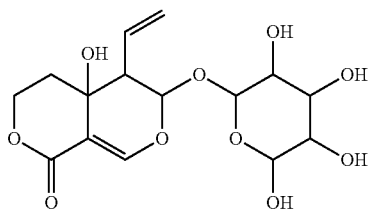 [SMILES: C=CC1C(OC2OC(O)C(O)C(O)C2O)OC=C2C(=O)OCCC21O]

Non-limiting examples of the keratinocyte growth factor stimulant include a purified (purity of at least 95%) or enriched extracts of swertiamarin. For example, swertiamarin is one of many compounds that may be isolated from species of *Swertia* including *Swertia chirata* and *Swertia milensis*. Swertiamarin may also be isolated from other plants of the family Gentianaceae, e.g., some species of the genus *Gentiana* and *Centaurium*.

In some embodiments, the keratinocyte growth factor stimulant imparts one or more therapeutic properties, including wound healing, hypoglycemic, antipyretic, antiparasitic, and antibacterial properties. For example, in traditional medicine, the species *Swertia chirata* (also known under the name of *Swertia chirayita*), which is native to the Himalayas and used in Ayurveda, has been used to prepare powders which are administered as an infusion, decoction or dye, for one or more of these therapeutic properties. Plants of the genus *Swertia* have been shown to include a large number of xanthonoid, alkaloid, terpenoid, flavonoid and iridoid compounds, potentially having biological activity, as discussed in WO 2015/136198, citing Brahmachari et al., CHEMISTRY & BIODIVERSITY Vol. 1 (2004) 1627-1651, and its English machine translation by the World Intellectual Property Organization [https://patentscope.wipo.int/search/en/detail.jsf?docId=WO2015136198&recNum=1&max Rec=&office=&prevFilter=&sortOption=&queryString=&tab=PCTDescription], which was attached as an Appendix in U.S. Provisional Application No. 62/327,232, the entire content of all of which documents, provisional application and Appendix is incorporated herein by reference. In some embodiments, the keratinocyte growth factor stimulant imparts one or more of anti-diabetic, anti-gastric, analgesic, antimicrobial, and anti-cholesterol effects. The keratinocyte growth factor stimulant according to embodiments of the present invention can be any suitable swertiamarin, including but not limited to a purified form, an extract of *Swertia* (including *Swertia chirata* and *Swertia milensis*), and combinations thereof. A non-limiting example of a suitable keratinocyte growth factor stimulant includes SWT-7™ available from Lucas Meyer Cosmetics, USA, described in the SWT-7™ product brochure available from Lucas Meyer Cosmetics, USA and attached as an Appendix to U.S. Provisional Application No. 62/327,232, the entire content of which product brochure, provisional application and Appendix is incorporated herein by reference. Some alternative swertiamarins are also described in WO 2015/136198, which was attached as an Appendix to U.S. Provisional Application No. 62/327,232, the entire content of which WO application, provisional application and Appendix is incorporated herein by reference.

The keratinocyte growth factor stimulant can reduce the appearance of wrinkles and skin roughness, promoting even skin tone and texture, in a short period of time. For example, Lucas Meyer Cosmetics has reported results from a double-blind test versus a placebo under dermatological control, in which 17 volunteers applied the placebo on one side of their face and a cream containing the SWT-7™ on the other side of the face, twice a day, for 28 days. Lucas Meyer Cosmetics analyzed the number of wrinkles and skin texture with numerical pictures and Visia CR filter after 7 and 28 days. At Day 7, Lucas Meyer Cosmetics reports that the observed maximum wrinkle reduction was up to 53%, the observed maximum skin roughness reduction was up to 42%, and 87% of the subjects reported a positive response after 28 days. According to Lucas Meyer Cosmetics, SWT-7™ blurs the appearance of vertical wrinkles after 7 days, and enhances the appearance of wrinkles and skin texture after 7 days, both building effect over time. Reduction in lip contour wrinkles was also reportedly observed after 7 days.

In some embodiments, the active constituent complex may include about 0.5-15 wt % of the keratinocyte growth factor stimulant. In some embodiments, the active constituent complex may include about 0.8-14 wt % of the keratinocyte growth factor stimulant. For example, in some embodiments, the keratinocyte growth factor stimulant may be present in the active constituent complex in an amount of about 0.96 wt %, 13.16 wt %, or 13.51 wt % based on the total weight of the active constituent complex.

As discussed above, the active constituent complex according to embodiments of the present invention also includes an active carrier. The active carrier is a multifunctional chemical constituent that enhances the bioavailability of the active constituent complex. For example, the active carrier, according to embodiments of the present invention, assists in penetration of the active constituent complex through the pores of the skin. The active carrier, according to some embodiments, possesses good skin moisturizing activity. The active carrier also reduces emulsion particle sizes, which helps to achieve better stability of the active constituent complex. In some embodiments of the present invention, the active carrier improves the aesthetic appeal of the composition. In some embodiments, the active carrier works synergistically with preservatives. In some embodiments, the active carrier improves the water resistance of the active constituent complex, enhancing the activity of the active constituent complex to be incorporated in, e.g., a sunscreen formulation. In some embodiments, the active carrier promotes skin repair and restructure. In some embodiments, the active carrier acts as an anti-wrinkle agent. In some embodiments, the active carrier exhibits broad-spectrum antimicrobial activity. In some embodiments, the active carrier possesses good solvent and solubility properties.

Non-limiting examples of the active carrier include an aqueous solvents and organic solvents, for example, alcohols such as ethanol, propanediol, butylene glycol, isopropanol, glycerin, and mixtures thereof. In some embodiments, the active carrier may include Pentylene Glycol, Ethoxydiglycol, Bis-Ethoxydiglycol Cyclohexane 1,4-Dicarboxylate, Dipalmitoyl Hydroxyproline, Potassium Palmitoyl Hydrolyzed Wheat Protein, Glyceryl Stearate, Cetearyl Alcohol, Potassium Lauroyl Wheat Amino Acids, Palm Glycerides, Capryloyl Glycine, Potassium Palmitoyl Hydrolyzed Oat Protein, Behenyl Alcohol, Palm Glycerides, Sodium Stearoyl Glutamate, Sucrose Palmitate, Polyglyceryl-3 Sorbityl Linseedate, or a combination thereof. In some embodiments, for example, a suitable active carrier includes Hydrolite® 5 available from Symrise AG, Germany, described in the Hydrolite® 5 product brochure available from Symrise AG and attached as an Appendix to U.S. Provisional Application No. 62/327,232, the entire content of which product brochure, provisional application and Appendix is incorporated herein by reference. Other non-limiting examples of suitable active carriers include Transcutol® CG available from Gattefossé SAS, France; Neosolue-Aqulio available from Nippon Fine Chemical Co., Ltd., Japan; SEPILIFT™ DPHP available from SEPPIC S.A., France; and PHYTOCREAM®2000, NANO-CREAM®, HITECREAM®3000, and EWOCREAM® available from Sinerga, Italy, described in their respective product brochures available from Gattefosséе SAS, Nippon Fine Chemical Co., SEPPIC S.A. and Sinerga and attached as an Appendix to U.S. Provisional Application No. 62/327,232, the entire content of which product brochures, provisional application and Appendix is incorporated herein by reference.

In some embodiments, the active constituent complex may include about 50-98 wt % of the active carrier. In some embodiments, the active constituent complex may include about 52-97 wt % of the active carrier. For example, in some embodiments, the active carrier may be present in the active constituent complex in an amount of about 52.63 wt %, 54.05 wt %, or 96.15 wt % based on the total weight of the active constituent complex.

According to embodiments of present invention, the active constituent complex can be incorporated into, and provided in, various compositions, such as in the form of emulsions (e.g., creams), gels, lotions, repairing cleansers, serums, eye creams, night moisturizers, and day lotions. The compositions including the active constituent complex y may also be in anhydrous form, such as in the form of ointments, gels, or serums.

Compositions that include the active constituent complex according to embodiments of the present invention may contain other components or additives that are typically used in skincare compositions, such as, for example, thickeners, emulsion stabilizers, emulsifiers, emollients, conditioners, humectants, moisturizers, preservatives, antioxidants, pH adjusters, surfactants, fragrances, etc. In some embodiments, the compositions may further include at least one additional cosmetic agent, such as a vitamin, sunscreen, anti-aging agent, anti-wrinkle agent, anti-oxidant, anti-redness agent, moisturizing agent, exfoliating agent, or a combination thereof.

Non-limiting examples of suitable anti-oxidant additives include *Olea Europaea* (Olive) Fruit Extract, *Terminalia Ferdinandiana* (Kakadu Plum) Fruit Extract, soy isoflavones, and *Juglans Regia* (Walnut) Seed Extract. In some embodiments, the anti-oxidant may also act as an anti-wrinkle agent. Non-limiting examples of suitable antioxidants include OPEXTAN® available from Indena S.p.A., Italy; Superox-C™ available from Lucas Meyer Cosmetics, USA; Soy isoflavones available from Sabinsa Corporation, USA; and Gatuline® Age Defense$^2$ available from Gattefossé SAS, France, described in their respective product brochures available from Indena S.p.A., Lucas Meyer Cosmetics, Sabinsa Corporation, and Gattefossé SAS and attached as an Appendix to U.S. Provisional Application No. 62/327,232, the entire content of which product brochure, provisional application and Appendix is incorporated herein by reference.

Nonlimiting examples of suitable anti-wrinkle agents and/or antioxidants that also act as anti-wrinkle agents include ARGIRELINE® peptide and snap-8 available from Lipotec SAU, Spain; and Dolcévia® available from Sinerga S.p.A., Italy, described in their respective product brochures available from Lipotec SAU and Sinerga S.p.A. and attached as an Appendix to U.S. Provisional Application No. 62/327,232, the entire content of which product brochures, provisional application and Appendix is incorporated herein by reference.

The compositions according to embodiments of the invention may be prepared according to conventional methods that are well-known to those of ordinary skill in the art.

The following Examples are provided for illustrative purposes only, and do not limit the scope of the embodiments of the present invention.

Example 1

| Repairing Cleanser | |
| --- | --- |
| INCI Name | Wt/Wt % |
| Dipotassium Glycyrrhizinate | 0.01 |
| Pentylene Glycol | 1.00 |
| Glycerin (and) Water (and) Methylglucoside Phosphate (and) Copper Lysinate/Prolinate | 0.01 |
| *Echinacea Purpurea* Extract | 0.01 |
| Isopropyl Palmitate (and) Lecithin (and) Water (and) *Swertia Chirata* Extract | 0.01 |
| Glycerin | [ ] |
| Sodium Hydroxide | [ ] |

Example 2

| Serum | |
| --- | --- |
| INCI Name | Wt/Wt % |
| Dipotassium Glycyrrhizinate | 0.10 |
| Pentylene Glycol | 2.00 |
| Glycerin (and) Water (and) Methylglucoside Phosphate (and) Copper Lysinate/Prolinate | 1.00 |
| *Echinacea Purpurea* Extract | 0.10 |
| Isopropyl Palmitate (and) Lecithin (and) Water (and) *Swertia Chirata* Extract | 0.50 |
| Glycerin | [ ] |
| Retinol | [ ] |
| Ceramide 3 | [ ] |
| Cetyl Palmitate | [ ] |
| Polysorbate 20 | [ ] |
| Sodium Hydroxide | [ ] |

A serum including the active constituent complex according to embodiments of the present invention may reduce sebum production. In some embodiments, the serum may include about 2.0-4.5 wt % of the active constituent complex. For example, in some embodiments, the active constituent complex may be present in the serum in an amount of about 3.7 wt % based on the total weight of the serum. In some embodiments, the serum may contain p-REFINYL® available from Silab, France, described in the p-REFINYL® product brochure available from Silab and attached as an Appendix to U.S. Provisional Application No. 62/327,232, the entire content of which product brochure, provisional application and Appendix is incorporated herein by reference. The serum according to some embodiments may stimulate the expression of collagen I, reinforcing dermal support structures and thus limiting pore wall thickening. In some embodiments, the serum significantly reduces pore area. In some embodiments, the serum tightens the pores, smooths the skin grain, and limits shininess of the skin for a more uniform and radiant complexion. In some embodiments, the serum contains KemSpheres R available from Oberhausen Technology Center (OTC) GmbH, Germany, described in the KemSpheres R product brochure available online at http://www.aerreita.it/sites/default/files/files/brochure/KemSpheres_A3_112010_0.pdf, the entire content of which is incorporated herein by reference. For example, in some embodiments, as described in the KemSpheres product brochure, the KemSpheres may include *Glycine Soja* Oil, Aqua, Glycerin, Cera Alba, Retinol, Laureth-23, Trideceth-6 Phosphate, Phenoxyethanol, Triethanolamine, and Ceramide-3. In some embodiments, the serum controls the release of retinol and enhances its bioavailability, thereby improving performance. In some embodiments, the serum reduces both wrinkles and fine lines. In some embodiments, the serum increases collagen production and skin thickness, improves elasticity, diminishes acne, increases skin hydration, and/or stimulates skin repair.

Example 3

| Eye Cream | |
|---|---|
| INCI Name | Wt/Wt % |
| Dipotassium Glycyrrhizinate | 0.20 |
| Pentylene Glycol | 2.00 |
| Glycerin (and) Water (and) Methylglucoside Phosphate (and) Copper Lysinate/Prolinate | 1.00 |
| *Echinacea Purpurea* Extract | 0.10 |
| Isopropyl Palmitate (and) Lecithin (and) Water (and) *Swertia Chirata* Extract | 0.50 |
| Glycerin | [ ] |
| *Butyrospermum Parkii* (Shea) Butter | [ ] |
| Niacinamide | [ ] |
| Sodium Hydroxide | [ ] |

An eye cream including the active constituent complex according to embodiments of the present invention may reduce under-eye circles. In some embodiments, the eye cream may include about 2.0-4.5 wt % of the active constituent complex. For example, in some embodiments, the active constituent complex may be present in the eye cream in an amount of about 3.8 wt % based on the total weight of the eye cream. For example, Sederma, France has reported a reduction in under-eye circles in more than 60% of volunteers using Haloxyl™ available from Sederma, France. Haloxyl™ is described in the Haloxyl™ product brochure available from Sederma and attached as an Appendix to U.S. Provisional Application No. 62/327,232, the entire content of which product brochure, provisional application and Appendix is incorporated herein by reference. In particular, Sederma conducted an in vivo study in which 22 female volunteers applied Haloxyl™ to the contour of one eye in the form of a gel containing 2% Haloxyl™ for 56 days, and applied placebo on the other eye. The anti-dark circle effect was assessed by image analysis and measurement of the color parameters (L,a,b system). Sederma reports improvements in the reduction of under-eye circles in 63% of the volunteers for Δb covering a spectrum of b−(blue) to b+(yellow), and 72% for Δa covering a spectrum of a−(green) to a+(red). Based on the same testing, Sederma reports that red and blue colors of the dark circles significantly decreased by 19%, as discussed in the Haloxyl™ product brochure.

An eye cream including the active constituent complex according to embodiments of the present invention may reduce under-eye bags. In some embodiments, the eye cream may include about 2.0-4.5 wt % of the active constituent complex. For example, in some embodiments, the active constituent complex may be present in the eye cream in an amount of about 3.8 wt % based on the total weight of the eye cream. For example, Sederma reported a 65% reduction in under-eye bags after 28 days of treatment using Eyeliss™ available from Sederma, France. Eyeliss™ is described in the Eyeliss™ product brochure available from Sederma and attached as an Appendix to U.S. Provisional Application No. 62/327,232, the entire content of which product brochure, provisional application and Appendix is incorporated herein by reference. In particular, Sederma tested 20 female volunteers, aged between 40 and 60 with chronic bags under the eyes, who have applied Eyeliss™ (3% in gel form) for 56 days. Based on a morphometric study using a software that measures the distance between the surface of the bag before treatment and the surface after the treatment, Sederma reports a reduction of bag volume in 70% of the volunteers after 56 days. Also, Sederma reports self-evaluation results in which 62% of the volunteers experienced eye contour smoothing; 52% experienced reduction in the bags, and 52% experienced a decongestant effect. The eye serum according to embodiments of the invention helps to prevent and fight bags under the eyes as well as to smooth the appearance of fine lines by firming and toning the skin.

Example 4

| Night Moisturizer | |
|---|---|
| INCI Name | Wt/Wt % |
| Dipotassium Glycyrrhizinate | 0.20 |
| Pentylene Glycol | 2.00 |
| Glycerin (and) Water (and) Methylglucoside Phosphate (and) Copper Lysinate/Prolinate | 1.00 |
| *Echinacea Purpurea* Extract | 0.10 |
| Isopropyl Palmitate (and) Lecithin (and) Water (and) *Swertia Chirata* Extract | 0.50 |
| Glycerin | [ ] |
| *Butyrospermum Parkii* (Shea) Butter | [ ] |
| Xylitylglucoside | [ ] |
| Anhydroxylitol | [ ] |
| Xylitol | [ ] |

A night moisturizer including the active constituent complex according to embodiments of the present invention may provide a natural anti-oxidant effect. In some embodiments, the night moisturizer may include about 2.0-4.5 wt % of the active constituent complex. For example, in some embodiments, the active constituent complex may be present in the night moisturizer in an amount of about 3.8 wt % based on the total weight of the night moisturizer. In some embodiments, the night moisturizer may contain Rosamox™ available from Kemin Industries, USA; AcquaCell available from Barnet Products Corp, USA, ARG-HA 1% available from ARGAN Co., USA, or a combination thereof. Rosamox™, AcquaCell and ARG-HA are described in their respective product brochures available from Kemin Industries, Barnet Products, and Argan Co. and attached as an Appendix to U.S. Provisional Application No. 62/327,232, the entire content of which product brochures, provisional application and Appendix is incorporated herein by reference. In some embodiments, the night moisturizer boosts the healthy and youthful appearance of skin elasticity. In some embodiments, the night moisturizer smooths and conditions the skin for a soft feeling, providing well-hydrated skin. In some embodiments, the night moisturizer may provide daily protection for the skin, and provide a healthy skin barrier integrity against blue light external aggression. In some embodiments, the night moisturizer may provide resistance to skin reddening after sun exposure. In some embodiments, the night moisturizer may provide 24 hours of skin hydration with one application. In some embodiments, the night moisturizer may significantly reduce fine lines, in as little as 2 hours of treatment. In some embodiments, the moisture in the skin may be increased by 50%. In some embodiments, the dryness may decrease by 60%. In some embodiments, skin cohesion may increase by 50%. In some embodiments, flakiness of the skin may be reduced by over 60% in as little as 10 days. In some embodiments, the night moisturizer including the active constituent complex may improve the skin's ability to absorb and hold moisture. In some embodiments, the night moisturizer strengthens the skin's barrier for softer, smoother, and/or plumper looking skin. In some embodiments, the night moisturizer provides anti-oxidant and anti-inflammatory benefits.

Example 5

| Daily Lotion SPF 50 | |
|---|---|
| INCI Name | Wt/Wt % |
| Dipotassium Glycyrrhizinate | 0.20 |
| Pentylene Glycol | 2.00 |
| Glycerin (and) Water (and) Methylglucoside Phosphate (and) Copper Lysinate/Prolinate | 1.00 |
| *Echinacea Purpurea* Extract | 0.10 |
| Isopropyl Palmitate (and) Lecithin (and) Water (and) *Swertia Chirata* Extract | 0.50 |
| Titanium Dioxide | [ ] |
| Zinc Oxide | [ ] |
| Glycerin | [ ] |

As used herein, the term "sign of aging" refers to any change or modification in the visual appearance or physiological properties of the skin, particularly due to aging or ultraviolet radiation exposure (photoaging). Non-limiting examples of signs of aging include thinning of the skin, appearance of fine lines or wrinkles, increased depth of wrinkles, sagging skin, loss of luminance of the skin, age spots, dark circles around the eyes, skin density loss, loss of firmness of the skin, loss of skin tone, loss of elasticity of the skin, increased roughness of the skin, and loss of smoothness of the skin. The terms, "treat," "treating," "treatment" and like terms refer to preventing, reversing, slowing, delaying, stopping, curing, correcting, mitigating, blurring, making less visible, reducing the appearance, or eliminating a physiological condition or symptom, such as a sign or signs of aging.

Although various embodiments of the invention have been described, additional modifications and variations will be apparent to those of ordinary skill in the art. For example, the described compositions may have additional components, which may be present in various suitable amounts, for example, other additives suitable to improve strength, impart a fragrance, and/or otherwise modify the properties of the composition. As such, the present disclosure is not limited to the embodiments specifically described, and the complexes and compositions may be modified without departing from the spirit and scope of the disclosure.

Throughout the text and claims, any use of the word "about" reflects the penumbra of variation associated with measurement, significant figures, and interchangeability, all as understood by a person having ordinary skill in the art to which this invention pertains. Further, a used herein, the term "substantially" is used as a term of approximation and not as a term of degree, and is intended to account for normal variations and deviations in the measurement or assessment of various parameters of the complexes and compositions (e.g., in the description of physical or chemical properties of various components and in the description of amounts of various components).

What is claimed is:

1. A topical skincare composition for application to the skin of a human, the skincare composition consisting essentially of:
a primary constituent complex consisting essentially of purified swertiamarin, pentylene glycol, dipotassium glycyrrhizinate, methylglucoside phosphate, and *Echinacea purpurea*, the primary constituent complex being present in the skincare composition in an amount effective to increase skin thickness, diminish the appearance of wrinkles and improve elasticity of the skin.

2. The skincare composition according to claim 1, wherein the pentylene glycol is present in the primary constituent complex in an amount of about 50 to 98% by weight based on 100% by weight of the primary constituent complex.

3. The skincare composition according to claim 1, wherein the dipotassium glycyrrhizinate is present in the primary constituent complex in an amount of about 0.5-6.0% by weight based on 100% by weight of the primary constituent complex.

4. The skincare composition according to claim 1, wherein the methylglucoside phosphate is present in the primary constituent complex in an amount of about 0.5 to 35% by weight based on 100% by weight of the primary constituent complex.

5. The skincare composition according to claim 1, wherein the *Echinacea purpurea* is present in the primary constituent complex in an amount of about 0.5 to 3.5% by weight based on 100% by weight of the primary constituent complex.

6. The skincare composition according to claim 1, wherein purified swertiamarin is present in the primary constituent complex in an amount of about 0.5-15% by weight based on 100% by weight of the primary constituent complex.

7. The skincare composition according to claim 1, wherein the primary constituent complex is present in the skincare composition in an amount of about 0.5 wt % to about 4.5 wt %.

8. The skincare composition according to claim 1, wherein the skincare composition is a lotion, a gel, an emulsion, a cleanser, a serum, an ointment, a repairing cleanser, an eye cream, a night moisturizer or a day lotion.

9. A topical skincare composition for application to the skin of a human, the skincare composition consisting essentially of:
a primary constituent complex consisting essentially of purified swertiamarin, pentylene glycol, dipotassium glycyrrhizinate, methylglucoside phosphate, and *Echinacea purpurea*, the primary constituent complex being present in the skincare composition in an amount effective to increase skin thickness, diminish the appearance of wrinkles and improve elasticity of the skin; and
one or more cosmeceutically acceptable additives selected from the group consisting of Lens *Esculenta* (Lentil) Seed Extract, *Helianthus Annus* (Sunflower)

Seed Oil, *Rosmarinus Officinalis* (Rosemary) Leaf Extract, *Citrullus lanatus* (Watermelon) Fruit Extract, *Pyrus Malus* (Apple) Fruit Extract, *Olea Europaea* (Olive) Fruit Extract, *Terminalia Ferdinandiana* (Kakadu Plum) Fruit Extract, soy isoflavones, *Juglans Regia* (Walnut) Seed Extract, Glycerin, water, Ethoxydiglycol, Bis-Ethoxydiglycol Cyclohexane 1,4-Dicarboxylate, ethanol, propanediol, butylene glycol, isopropanol, Dipalmitoyl Hydroxyproline, Potassium Palmitoyl Hydrolyzed Wheat Protein, Glyceryl Stearate, Cetearyl Alcohol, Potassium Lauroyl Wheat Amino Acids, Palm Glycerides, Capryloyl Glycine, Potassium Palmitoyl Hydrolyzed Oat Protein, Behenyl Alcohol, Sodium Stearoyl Glutamate, Sucrose Palmitate, Polyglyceryl-3 Sorbityl Linseedate, alpha-Bisabolol, Allantoin, Sea Whip Extract, *Chamomilla Recutita* (*Matricaria*) Extract, Tocopheryl Acetate, *Camellia Sinensis* Leaf Extract, *Curcuma Longa* (Turmeric) Root Extract, *Avena Sativa* (Oat) Kernel Extract, *Magnolia Officinalis* Bark Extract, *Vitis Vinifera* (Grape) Seed Extract, *Zingiber Officinale* (Ginger) Root Extract, *Inula Crithmoide* Flower Extract, *Inula Crithmoide* Leaf Extract, Collagen Prepeptide, Madecassoside, Asiaticoside, Cichoric acid, Resveratrol, Trifluoroacetyl Tripeptide-2, Copper Lysinate, Copper Prolinate, Isopropyl Palmitate, Lecithin, Sodium Hydroxide, *Glycine Soja* Oil, Cera Alba, Retinol, Laureth-23, Trideceth-6 Phosphate, Phenoxyethanol, Triethanolamine, Ceramide-3, *Butyrospermum Parkii* (Shea) Butter, Niacinamide, Steareth-20, N-Hydroxysuccinimide, Chrysin, Palmitoyl Oligopeptide, Palmitoyl Tetrapeptide-7, Hesperidin Methyl Chalcone, Dipeptide-2, Xylitylglucoside, Anhydroxylitol, Xylitol, Sodium PCA, Sodium Lactate, Sodium Hyaluronate, Titanium Dioxide, Zinc Oxide, and combinations thereof.

10. The skincare composition according to claim 9, wherein the primary constituent complex is present in the skincare composition in an amount of about 0.5 wt % to about 4.5 wt %.

11. The skincare composition according to claim 9, wherein the one or more cosmeceutically acceptable additives comprises a combination of Glycerin, water, Copper Lysinate/Prolinate, Isopropyl Palmitate, lecithin, and sodium hydroxide.

12. The skincare composition according to claim 11, wherein the skincare composition is a repairing cleanser.

13. The skincare composition according to claim 9, wherein the one or more cosmeceutically acceptable additives comprises a combination of Glycerin, water, Copper Lysinate/Prolinate, Isopropyl Palmitate, lecithin, Retinol, Ceramide 3, Cetyl Palmitate, Polysorbate 20, and sodium hydroxide.

14. The skincare composition according to claim 13, wherein the skincare composition is a serum.

15. The skincare composition according to claim 9, wherein the one or more cosmeceuteically acceptable additives comprises a combination of Glycerin, water, Copper Lysinate/Prolinate, isopropyl Palmitate, lecithin, *Butyrospermum Parkii* (Shea) Butter, Niacinamide, and sodium hydroxide.

16. The skincare composition according to claim 15, wherein the skincare composition is an eye cream.

17. The skincare composition according to claim 9, wherein the one or more cosmeceutically acceptable additives comprises a combination of Glycerin, water, Copper Lysinate/Prolinate, Isopropyl Palmitate, lecithin, *Butyrospermum Parkii* (Shea) Butter, xylitylglucoside, anhydroxylitol, and xylitol.

18. The skincare composition according to claim 17, wherein the skincare composition is a night moisturizer.

19. The skincare composition according to claim 9, wherein the one or more cosmeceutically acceptable additives comprises a combination of Glycerin, water, Copper Lysinate/Prolinate, Isopropyl Palmitate, lecithin, Titanium Dioxide, and Zinc Oxide.

20. The skincare composition according to claim 19, wherein the skincare composition is a daily lotion providing a sun protection factor.

* * * * *